United States Patent
Vitek et al.

(10) Patent No.: US 9,177,543 B2
(45) Date of Patent: Nov. 3, 2015

(54) ASYMMETRIC ULTRASOUND PHASED-ARRAY TRANSDUCER FOR DYNAMIC BEAM STEERING TO ABLATE TISSUES IN MRI

(75) Inventors: Shuki Vitek, Haifa (IL); Kobi Vortman, Haifa (IL)

(73) Assignee: InSightec Ltd., Tirat Carmel (IL)

( * ) Notice: Subject to any disclaimer, the term of this patent is extended or adjusted under 35 U.S.C. 154(b) by 595 days.

(21) Appl. No.: 12/869,024

(22) Filed: Aug. 26, 2010

(65) Prior Publication Data

US 2011/0066032 A1  Mar. 17, 2011

Related U.S. Application Data

(60) Provisional application No. 61/237,054, filed on Aug. 26, 2009.

(51) Int. Cl.
| | |
|---|---|
| A61B 8/00 | (2006.01) |
| G10K 11/34 | (2006.01) |
| A61N 7/02 | (2006.01) |
| B06B 1/06 | (2006.01) |
| G01S 15/89 | (2006.01) |
| A61N 7/00 | (2006.01) |

(52) U.S. Cl.
CPC .............. *G10K 11/345* (2013.01); *A61N 7/02* (2013.01); *B06B 1/0629* (2013.01); *B06B 1/0633* (2013.01); *G01S 15/8925* (2013.01); *G10K 11/346* (2013.01); *A61N 2007/0095* (2013.01); *G01S 15/8952* (2013.01)

(58) Field of Classification Search
CPC ... G10K 11/18; G10K 11/346; G10K 11/345; G01S 15/8927; A61N 2007/0095; A61N 7/02
USPC .............................................. 600/437; 601/2
See application file for complete search history.

(56) References Cited

U.S. PATENT DOCUMENTS

| | | |
|---|---|---|
| 2,795,709 A | 6/1957 | Camp |
| 3,142,035 A | 7/1964 | Harris |
| 3,559,159 A | 1/1971 | Harms et al. |
| 3,942,150 A | 3/1976 | Booth et al. |
| 3,974,475 A | 8/1976 | Burckhardt et al. |

(Continued)

FOREIGN PATENT DOCUMENTS

| | | |
|---|---|---|
| CN | 1744861 A | 3/2006 |
| CN | 1981708 A | 6/2007 |

(Continued)

OTHER PUBLICATIONS

Fronheiser et al., "3D Acoustic Radiation Force Impulse (ARFI) Imaging Using a 2D Matrix Array: Feasibility Study," Ultrasonics Symposium, pp. 1144-1147 (Oct. 2006).

(Continued)

*Primary Examiner* — Unsu Jung
*Assistant Examiner* — Serkan Akar
(74) *Attorney, Agent, or Firm* — Morgan, Lewis & Bockius LLP

(57) ABSTRACT

An asymmetric ultrasound transducer array may include multiple regions or groups of transducer elements. The regions may be configured to generate respective ultrasound beams with different capabilities, such as, e.g., focusing at varying focal depths and lateral steering, and/or focusing into different volumes.

20 Claims, 5 Drawing Sheets

(56) References Cited

U.S. PATENT DOCUMENTS

| | | |
|---|---|---|
| 3,992,693 A | 11/1976 | Martin et al. |
| 4,000,493 A | 12/1976 | Spaulding et al. |
| 4,052,723 A | 10/1977 | Miller |
| 4,074,564 A | 2/1978 | Anderson |
| 4,206,653 A | 6/1980 | Lemay |
| 4,211,132 A | 7/1980 | Nichols, III et al. |
| 4,221,132 A | 9/1980 | Poole |
| 4,307,613 A | 12/1981 | Fox |
| 4,339,952 A | 7/1982 | Foster |
| 4,441,486 A | 4/1984 | Pounds |
| 4,454,597 A | 6/1984 | Sullivan |
| 4,478,083 A | 10/1984 | Hassler et al. |
| 4,505,156 A | 3/1985 | Questo |
| 4,526,168 A | 7/1985 | Hassler et al. |
| 4,537,074 A | 8/1985 | Dietz |
| 4,549,533 A | 10/1985 | Cain et al. |
| 4,554,925 A | 11/1985 | Young |
| 4,586,512 A | 5/1986 | Do-huu et al. |
| 4,616,231 A | 10/1986 | Autrey et al. |
| 4,636,964 A | 1/1987 | Jacobs et al. |
| 4,646,756 A | 3/1987 | Watmough et al. |
| 4,647,808 A | 3/1987 | Shibuya |
| 4,662,222 A | 5/1987 | Johnson |
| 4,757,820 A | 7/1988 | Itoh |
| 4,817,614 A | 4/1989 | Hassler et al. |
| 4,823,053 A | 4/1989 | Mccracken et al. |
| 4,858,597 A | 8/1989 | Kurtze et al. |
| 4,858,613 A | 8/1989 | Fry et al. |
| 4,865,042 A | 9/1989 | Umemura et al. |
| 4,886,491 A | 12/1989 | Parisi et al. |
| 4,888,746 A | 12/1989 | Wurster et al. |
| 4,889,122 A | 12/1989 | Watmough et al. |
| 4,893,284 A | 1/1990 | Magrane |
| 4,893,624 A | 1/1990 | Lele |
| 4,937,767 A | 6/1990 | Reuschel et al. |
| 4,938,217 A | 7/1990 | Lele |
| 4,957,099 A | 9/1990 | Hassler |
| 5,015,929 A | 5/1991 | Cathignol et al. |
| 5,143,063 A | 9/1992 | Fellner |
| 5,165,412 A | 11/1992 | Okazaki |
| 5,172,343 A | 12/1992 | O'donnell |
| 5,186,175 A * | 2/1993 | Hirama et al. ............... 600/447 |
| 5,197,475 A | 3/1993 | Antich et al. |
| 5,209,221 A | 5/1993 | Riedlinger |
| 5,211,160 A | 5/1993 | Talish et al. |
| 5,247,935 A | 9/1993 | Cline et al. |
| 5,266,863 A | 11/1993 | Nonami et al. |
| 5,267,221 A | 11/1993 | Miller et al. |
| 5,269,307 A | 12/1993 | Fife et al. |
| 5,271,400 A | 12/1993 | Dumoulin et al. |
| 5,275,165 A | 1/1994 | Ettinger et al. |
| 5,291,890 A | 3/1994 | Cline et al. |
| 5,305,737 A | 4/1994 | Vago |
| 5,307,812 A | 5/1994 | Hardy et al. |
| 5,307,816 A | 5/1994 | Hashimoto et al. |
| 5,318,025 A | 6/1994 | Dumoulin et al. |
| 5,323,779 A | 6/1994 | Hardy et al. |
| 5,327,884 A | 7/1994 | Hardy et al. |
| 5,329,930 A | 7/1994 | Thomas, III et al. |
| 5,368,031 A | 11/1994 | Cline et al. |
| 5,368,032 A | 11/1994 | Cline et al. |
| 5,379,642 A | 1/1995 | Reckwerdt et al. |
| 5,388,461 A | 2/1995 | Rigby |
| 5,391,140 A | 2/1995 | Schaetzle et al. |
| 5,413,550 A | 5/1995 | Castel |
| 5,419,761 A | 5/1995 | Narayanan et al. |
| 5,435,312 A | 7/1995 | Spivey et al. |
| 5,443,068 A | 8/1995 | Cline et al. |
| 5,474,071 A | 12/1995 | Chapelon et al. |
| 5,477,736 A | 12/1995 | Lorraine |
| 5,485,839 A | 1/1996 | Aida et al. |
| 5,490,512 A * | 2/1996 | Kwon et al. ............... 600/447 |
| 5,490,840 A | 2/1996 | Uzgiris et al. |
| 5,507,790 A | 4/1996 | Weiss |
| 5,514,086 A | 5/1996 | Parisi et al. |
| 5,520,186 A * | 5/1996 | Deitrich ............... 600/437 |
| 5,520,188 A | 5/1996 | Hennige et al. |
| 5,520,612 A | 5/1996 | Winder et al. |
| 5,526,814 A | 6/1996 | Cline et al. |
| 5,527,273 A | 6/1996 | Manna et al. |
| 5,546,360 A | 8/1996 | Deegan |
| 5,549,638 A | 8/1996 | Burdette |
| 5,553,618 A | 9/1996 | Suzuki et al. |
| 5,573,497 A | 11/1996 | Chapelon |
| 5,582,578 A | 12/1996 | Zhong et al. |
| 5,590,653 A | 1/1997 | Aida et al. |
| 5,590,657 A | 1/1997 | Cain et al. |
| 5,601,526 A | 2/1997 | Chapelon et al. |
| 5,605,154 A | 2/1997 | Ries et al. |
| 5,606,971 A | 3/1997 | Sarvazyan |
| 5,617,371 A | 4/1997 | Williams |
| 5,617,857 A | 4/1997 | Chader et al. |
| 5,643,179 A | 7/1997 | Fujimoto |
| 5,662,170 A | 9/1997 | Donovan et al. |
| 5,665,054 A | 9/1997 | Dory |
| 5,666,954 A | 9/1997 | Chapelon et al. |
| 5,676,673 A | 10/1997 | Ferre et al. |
| 5,687,729 A | 11/1997 | Schaetzle |
| 5,694,936 A | 12/1997 | Fujimoto et al. |
| 5,711,300 A | 1/1998 | Schneider et al. |
| 5,718,226 A | 2/1998 | Riza |
| 5,722,411 A | 3/1998 | Suzuki et al. |
| 5,725,482 A | 3/1998 | Bishop |
| 5,728,062 A | 3/1998 | Brisken |
| 5,739,625 A | 4/1998 | Falcus |
| 5,743,863 A | 4/1998 | Chapelon |
| 5,752,515 A | 5/1998 | Jolesz et al. |
| 5,759,162 A | 6/1998 | Oppelt et al. |
| 5,762,616 A | 6/1998 | Talish |
| 5,769,790 A | 6/1998 | Watkins et al. |
| 5,769,879 A | 6/1998 | Richards et al. |
| 5,784,336 A | 7/1998 | Gopinathan et al. |
| 5,810,008 A | 9/1998 | Dekel et al. |
| 5,810,731 A | 9/1998 | Sarvazyan et al. |
| 5,817,021 A | 10/1998 | Reichenberger |
| 5,817,036 A | 10/1998 | Anthony et al. |
| 5,823,990 A | 10/1998 | Henley |
| 5,827,204 A | 10/1998 | Grandia et al. |
| 5,873,845 A | 2/1999 | Cline et al. |
| 5,884,631 A | 3/1999 | Silberg |
| 5,885,211 A | 3/1999 | Eppstein et al. |
| 5,891,040 A | 4/1999 | Grenon et al. |
| 5,897,495 A | 4/1999 | Aida et al. |
| 5,904,659 A | 5/1999 | Duarte et al. |
| 5,922,962 A * | 7/1999 | Ishrak et al. ............... 73/632 |
| 5,938,600 A | 8/1999 | Van Vaals et al. |
| 5,938,608 A | 8/1999 | Bieger et al. |
| 5,947,900 A | 9/1999 | Derbyshire et al. |
| 5,984,881 A | 11/1999 | Ishibashi et al. |
| 6,004,269 A | 12/1999 | Crowley et al. |
| 6,007,499 A | 12/1999 | Martin et al. |
| 6,013,048 A | 1/2000 | Podany et al. |
| 6,023,636 A | 2/2000 | Wendt et al. |
| 6,032,675 A | 3/2000 | Rubinsky |
| 6,033,375 A | 3/2000 | Brumbach |
| 6,036,644 A | 3/2000 | Schutt |
| 6,039,048 A | 3/2000 | Silberg |
| 6,042,556 A | 3/2000 | Beach et al. |
| 6,045,777 A | 4/2000 | Church et al. |
| 6,071,239 A | 6/2000 | Cribbs et al. |
| 6,088,295 A | 7/2000 | Altes |
| 6,106,511 A | 8/2000 | Jensen |
| 6,113,558 A | 9/2000 | Rosenschein et al. |
| 6,113,559 A | 9/2000 | Klopotek |
| 6,128,522 A | 10/2000 | Acker et al. |
| 6,128,958 A | 10/2000 | Cain |
| 6,135,960 A | 10/2000 | Holmberg |
| 6,135,971 A | 10/2000 | Hutchinson et al. |
| 6,142,939 A | 11/2000 | Eppstein et al. |
| 6,156,549 A | 12/2000 | Drewes et al. |
| 6,193,659 B1 | 2/2001 | Ramamurthy et al. |
| 6,217,530 B1 | 4/2001 | Martin et al. |
| 6,242,915 B1 | 6/2001 | Hurd |
| 6,246,895 B1 | 6/2001 | Plewes |

(56) References Cited

U.S. PATENT DOCUMENTS

| | | |
|---|---|---|
| 6,246,896 B1 | 6/2001 | Dumoulin et al. |
| 6,263,230 B1 | 7/2001 | Haynor et al. |
| 6,267,734 B1 | 7/2001 | Ishibashi et al. |
| 6,289,233 B1 | 9/2001 | Dumoulin et al. |
| 6,309,355 B1 | 10/2001 | Cain et al. |
| 6,317,619 B1 | 11/2001 | Boernert et al. |
| 6,322,527 B1 | 11/2001 | Talish |
| 6,334,846 B1 | 1/2002 | Ishibashi et al. |
| 6,350,245 B1 | 2/2002 | Cimino |
| 6,374,132 B1 | 4/2002 | Acker et al. |
| 6,392,330 B1 | 5/2002 | Zloter et al. |
| 6,397,094 B1 | 5/2002 | Ludeke et al. |
| 6,413,216 B1 | 7/2002 | Cain et al. |
| 6,419,648 B1 | 7/2002 | Vitek et al. |
| 6,424,597 B1 | 7/2002 | Bolomey et al. |
| 6,425,867 B1 | 7/2002 | Vaezy et al. |
| 6,428,477 B1 | 8/2002 | Mason |
| 6,428,532 B1 | 8/2002 | Doukas et al. |
| 6,433,464 B2 | 8/2002 | Jones |
| 6,461,314 B1 | 10/2002 | Pant et al. |
| 6,475,150 B2 | 11/2002 | Haddad |
| 6,478,739 B1 | 11/2002 | Hong |
| 6,503,204 B1 | 1/2003 | Sumanaweera et al. |
| 6,506,154 B1 | 1/2003 | Ezion et al. |
| 6,506,171 B1 | 1/2003 | Vitek et al. |
| 6,508,774 B1 | 1/2003 | Acker et al. |
| 6,511,064 B1 | 1/2003 | Phinney et al. |
| 6,511,428 B1 | 1/2003 | Azuma et al. |
| 6,522,142 B1 | 2/2003 | Freundlich |
| 6,523,272 B1 | 2/2003 | Morales |
| 6,524,251 B2 | 2/2003 | Rabiner et al. |
| 6,543,272 B1 | 4/2003 | Vitek |
| 6,554,826 B1 | 4/2003 | Deardorff |
| 6,559,644 B2 | 5/2003 | Froundlich et al. |
| 6,566,878 B1 | 5/2003 | Komura et al. |
| 6,582,381 B1 | 6/2003 | Yehezkeli et al. |
| 6,589,174 B1 | 7/2003 | Chopra et al. |
| 6,599,256 B1 | 7/2003 | Acker et al. |
| 6,612,988 B2 | 9/2003 | Maor et al. |
| 6,613,004 B1 | 9/2003 | Vitek et al. |
| 6,613,005 B1 | 9/2003 | Friedman et al. |
| 6,618,608 B1 | 9/2003 | Watkins et al. |
| 6,618,620 B1 | 9/2003 | Freundlich et al. |
| 6,626,854 B2 | 9/2003 | Friedman et al. |
| 6,626,855 B1 | 9/2003 | Weng et al. |
| 6,629,929 B1 | 10/2003 | Jago et al. |
| 6,645,162 B2 | 11/2003 | Friedman et al. |
| 6,652,461 B1 | 11/2003 | Levkovitz |
| 6,666,833 B1 | 12/2003 | Friedman et al. |
| 6,676,601 B1 | 1/2004 | Lacoste et al. |
| 6,676,602 B1 | 1/2004 | Barnes et al. |
| 6,679,855 B2 | 1/2004 | Horn et al. |
| 6,705,994 B2 | 3/2004 | Vortman et al. |
| 6,719,694 B2 | 4/2004 | Weng et al. |
| 6,733,450 B1 | 5/2004 | Alexandrov et al. |
| 6,735,461 B2 | 5/2004 | Vitek et al. |
| 6,761,691 B2 | 7/2004 | Tsuzuki |
| 6,770,031 B2 | 8/2004 | Hynynen et al. |
| 6,770,039 B2 | 8/2004 | Zhong et al. |
| 6,788,619 B2 | 9/2004 | Calvert |
| 6,790,180 B2 | 9/2004 | Vitek |
| 6,805,129 B1 | 10/2004 | Pless et al. |
| 6,824,516 B2 | 11/2004 | Batten et al. |
| 6,936,046 B2 | 8/2005 | Hissong et al. |
| 6,951,540 B2 | 10/2005 | Ebbini et al. |
| 6,961,606 B2 | 11/2005 | DeSilets et al. |
| 7,001,379 B2 | 2/2006 | Behl et al. |
| 7,077,820 B1 | 7/2006 | Kadziauskas et al. |
| 7,094,205 B2 | 8/2006 | Marmarelis |
| 7,128,711 B2 | 10/2006 | Medan et al. |
| 7,155,271 B2 | 12/2006 | Halperin et al. |
| 7,175,596 B2 | 2/2007 | Vitek et al. |
| 7,175,599 B2 | 2/2007 | Hynynen et al. |
| 7,264,592 B2 | 9/2007 | Shehada |
| 7,264,597 B2 | 9/2007 | Cathignol |
| 7,267,650 B2 | 9/2007 | Chow et al. |
| 7,344,509 B2 | 3/2008 | Hynynen et al. |
| 7,377,900 B2 | 5/2008 | Vitek et al. |
| 7,429,248 B1 | 9/2008 | Winder et al. |
| 7,452,357 B2 | 11/2008 | Vlegele et al. |
| 7,505,805 B2 | 3/2009 | Kuroda |
| 7,505,808 B2 | 3/2009 | Anderson et al. |
| 7,507,213 B2 | 3/2009 | Schultheiss et al. |
| 7,510,536 B2 | 3/2009 | Foley et al. |
| 7,511,501 B2 | 3/2009 | Wexler |
| 7,535,794 B2 | 5/2009 | Prus et al. |
| 7,553,284 B2 | 6/2009 | Vaitekunas |
| 7,603,162 B2 | 10/2009 | Danz et al. |
| 7,611,462 B2 | 11/2009 | Vortman et al. |
| 7,652,410 B2 | 1/2010 | Prus |
| 7,699,780 B2 | 4/2010 | Vitek et al. |
| 7,819,805 B2 | 10/2010 | Davies et al. |
| 8,002,706 B2 | 8/2011 | Vortman et al. |
| 8,057,408 B2 | 11/2011 | Cain et al. |
| 8,075,488 B2 | 12/2011 | Burton |
| 8,088,067 B2 | 1/2012 | Vortman et al. |
| 8,409,099 B2 | 4/2013 | Vitek et al. |
| 8,425,424 B2 | 4/2013 | Zadicario et al. |
| 8,608,672 B2 | 12/2013 | Vortman et al. |
| 8,617,073 B2 | 12/2013 | Prus et al. |
| 8,661,873 B2 | 3/2014 | Medan et al. |
| 8,932,237 B2 | 1/2015 | Vitek et al. |
| 2001/0031922 A1 | 10/2001 | Weng et al. |
| 2002/0016557 A1 | 2/2002 | Duarte et al. |
| 2002/0035779 A1 | 3/2002 | Krieg et al. |
| 2002/0082528 A1 | 6/2002 | Friedman et al. |
| 2002/0082589 A1 | 6/2002 | Friedman et al. |
| 2002/0095087 A1 | 7/2002 | Mourad et al. |
| 2002/0111552 A1 | 8/2002 | Maor et al. |
| 2002/0151790 A1 | 10/2002 | Abend |
| 2002/0161300 A1 | 10/2002 | Hoff et al. |
| 2002/0188229 A1 | 12/2002 | Ryaby |
| 2003/0004439 A1 | 1/2003 | Pant et al. |
| 2003/0055308 A1* | 3/2003 | Friemel et al. ............ 600/15 |
| 2003/0060820 A1 | 3/2003 | Maguire et al. |
| 2003/0187371 A1 | 10/2003 | Vortman et al. |
| 2004/0030251 A1 | 2/2004 | Ebbini et al. |
| 2004/0059265 A1 | 3/2004 | Candy et al. |
| 2004/0068186 A1 | 4/2004 | Ishida et al. |
| 2004/0082868 A1 | 4/2004 | Campbell et al. |
| 2004/0116809 A1 | 6/2004 | Chow et al. |
| 2004/0122316 A1 | 6/2004 | Satoh |
| 2004/0122323 A1 | 6/2004 | Vortman et al. |
| 2004/0143187 A1 | 7/2004 | Biagi et al. |
| 2004/0147919 A1 | 7/2004 | Behl et al. |
| 2004/0210134 A1 | 10/2004 | Hynynen et al. |
| 2004/0210135 A1 | 10/2004 | Hynynen et al. |
| 2004/0236253 A1 | 11/2004 | Vortman et al. |
| 2004/0236523 A1 | 11/2004 | Taylor |
| 2004/0267126 A1 | 12/2004 | Takeuchi |
| 2005/0033201 A1 | 2/2005 | Takahashi et al. |
| 2005/0096542 A1 | 5/2005 | Weng et al. |
| 2005/0131301 A1 | 6/2005 | Peszynski et al. |
| 2005/0154304 A1 | 7/2005 | Robinson |
| 2005/0199058 A1 | 9/2005 | Danz et al. |
| 2005/0203444 A1 | 9/2005 | Schonenberger et al. |
| 2005/0240126 A1 | 10/2005 | Foley et al. |
| 2005/0251046 A1 | 11/2005 | Yamamoto et al. |
| 2006/0052661 A1 | 3/2006 | Gannot et al. |
| 2006/0052701 A1 | 3/2006 | Carter et al. |
| 2006/0052706 A1 | 3/2006 | Hynynen et al. |
| 2006/0058671 A1 | 3/2006 | Vitek et al. |
| 2006/0058678 A1 | 3/2006 | Vitek et al. |
| 2006/0106300 A1 | 5/2006 | Seppenwoolde et al. |
| 2006/0173307 A1 | 8/2006 | Amara et al. |
| 2006/0173321 A1 | 8/2006 | Kubota et al. |
| 2006/0173385 A1 | 8/2006 | Lidgren et al. |
| 2006/0184034 A1 | 8/2006 | Haim et al. |
| 2006/0184069 A1 | 8/2006 | Vaitekunas |
| 2006/0206105 A1 | 9/2006 | Chopra et al. |
| 2006/0229594 A1 | 10/2006 | Francischelli et al. |
| 2006/0235302 A1 | 10/2006 | Grossman et al. |
| 2006/0253026 A1* | 11/2006 | Gueck et al. ............ 600/439 |
| 2007/0016039 A1 | 1/2007 | Vortman et al. |

(56) References Cited

U.S. PATENT DOCUMENTS

| | | |
|---|---|---|
| 2007/0055140 A1 | 3/2007 | Kuroda |
| 2007/0066897 A1 | 3/2007 | Sekins et al. |
| 2007/0073135 A1 | 3/2007 | Lee et al. |
| 2007/0098232 A1 | 5/2007 | Matula et al. |
| 2007/0167781 A1 | 7/2007 | Vortman et al. |
| 2007/0167798 A1 | 7/2007 | Cai et al. |
| 2007/0197918 A1 | 8/2007 | Vitek et al. |
| 2007/0219470 A1 | 9/2007 | Talish et al. |
| 2007/0239062 A1 | 10/2007 | Chopra et al. |
| 2007/0265560 A1 | 11/2007 | Soltani et al. |
| 2007/0276237 A1 | 11/2007 | Li |
| 2008/0027342 A1 | 1/2008 | Rouw et al. |
| 2008/0030104 A1 | 2/2008 | Prus |
| 2008/0031090 A1 | 2/2008 | Prus et al. |
| 2008/0033278 A1 | 2/2008 | Assif |
| 2008/0082026 A1 | 4/2008 | Schmidt et al. |
| 2008/0103558 A1 | 5/2008 | Wenzel et al. |
| 2008/0108900 A1 | 5/2008 | Lee et al. |
| 2008/0125660 A1 | 5/2008 | Yao et al. |
| 2008/0183077 A1 | 7/2008 | Moreau-Gobard et al. |
| 2008/0228081 A1 | 9/2008 | Becker et al. |
| 2008/0312562 A1 | 12/2008 | Routh et al. |
| 2009/0088623 A1 | 4/2009 | Vortman et al. |
| 2009/0093721 A1 | 4/2009 | Katsuyama |
| 2009/0096450 A1 | 4/2009 | Roland |
| 2009/0118619 A1 | 5/2009 | Oshiki |
| 2010/0030076 A1 | 2/2010 | Vortman et al. |
| 2010/0056962 A1 | 3/2010 | Vortman et al. |
| 2010/0125193 A1 | 5/2010 | Zadicario |
| 2010/0179425 A1 | 7/2010 | Zadicario |
| 2010/0268088 A1 | 10/2010 | Prus et al. |
| 2010/0274130 A1 | 10/2010 | Anand et al. |
| 2010/0318002 A1 | 12/2010 | Prus et al. |
| 2011/0094288 A1 | 4/2011 | Medan et al. |
| 2011/0130663 A1 | 6/2011 | Raju et al. |
| 2011/0137147 A1 | 6/2011 | Skliar et al. |
| 2011/0251527 A1 | 10/2011 | Kushculey et al. |
| 2011/0270075 A1 | 11/2011 | Vitek et al. |
| 2011/0270136 A1 | 11/2011 | Vitek et al. |
| 2012/0083695 A1 | 4/2012 | Napolitano et al. |
| 2013/0077441 A1 | 3/2013 | Ramamurthy et al. |
| 2014/0112095 A1 | 4/2014 | Medan et al. |

FOREIGN PATENT DOCUMENTS

| | | |
|---|---|---|
| CN | 101137329 A | 3/2008 |
| CN | 102348481 A | 2/2012 |
| CN | 102946945 A | 2/2013 |
| CN | 103140261 A | 6/2013 |
| DE | 4345308 | 2/2001 |
| DE | 10102317 A1 | 8/2002 |
| EP | 151073 A2 | 8/1985 |
| EP | 174920 A1 | 3/1986 |
| EP | 272347 A1 | 6/1988 |
| EP | 0320303 | 6/1989 |
| EP | 450334 A2 | 10/1991 |
| EP | 462311 A1 | 12/1991 |
| EP | 467690 A2 | 1/1992 |
| EP | 0558029 | 9/1993 |
| EP | 0558029 A3 | 9/1994 |
| EP | 627206 A2 | 12/1994 |
| EP | 734742 A2 | 10/1996 |
| EP | 875203 A2 | 11/1998 |
| EP | 1132054 | 9/2001 |
| EP | 1582886 A1 | 10/2005 |
| EP | 151073 | 11/2005 |
| EP | 1774920 | 4/2007 |
| EP | 1790384 | 5/2007 |
| EP | 1936404 | 6/2008 |
| EP | 2429656 A1 | 3/2012 |
| EP | 2440292 A1 | 4/2012 |
| EP | 2489034 A2 | 8/2012 |
| EP | 2563475 A2 | 3/2013 |
| EP | 2563476 A2 | 3/2013 |
| EP | 2429656 B1 | 6/2013 |
| EP | 2563475 B1 | 8/2014 |
| EP | 1796545 B1 | 10/2014 |
| FR | 2692999 A1 | 12/1993 |
| FR | 2806611 A1 | 8/2002 |
| GB | 2019565 A | 10/1979 |
| JP | 5-92008 | 4/1993 |
| JP | 7-184907 A | 7/1995 |
| JP | 7-231895 | 9/1995 |
| JP | 7-313518 | 12/1995 |
| JP | 11313833 | 11/1999 |
| JP | 00/166940 | 6/2000 |
| JP | 01/516075 | 9/2001 |
| JP | 02/530145 | 9/2002 |
| JP | 2006-503653 T | 2/2006 |
| JP | 5066569 B2 | 11/2012 |
| JP | 5087007 B2 | 11/2012 |
| WO | WO-91/00059 | 1/1991 |
| WO | 91/15999 A1 | 10/1991 |
| WO | 91/19332 A1 | 12/1991 |
| WO | 93/15415 A1 | 8/1993 |
| WO | WO-95/14505 | 6/1995 |
| WO | 97/17018 A1 | 5/1997 |
| WO | WO-98/52465 | 11/1998 |
| WO | WO-00/31614 | 6/2000 |
| WO | 00/78232 A1 | 12/2000 |
| WO | 01/43640 A2 | 6/2001 |
| WO | 01/59337 A3 | 8/2001 |
| WO | WO-01/58337 | 8/2001 |
| WO | WO-01/66189 | 9/2001 |
| WO | 01/80708 A2 | 11/2001 |
| WO | WO-01/80709 | 11/2001 |
| WO | 01/80708 A3 | 3/2002 |
| WO | WO-02/43805 | 6/2002 |
| WO | WO-02/44753 | 6/2002 |
| WO | WO-02/058791 | 8/2002 |
| WO | WO-03/013654 | 2/2003 |
| WO | 03/070105 A1 | 8/2003 |
| WO | WO-03/097162 | 11/2003 |
| WO | WO-03/098232 | 11/2003 |
| WO | 2004/021044 A1 | 3/2004 |
| WO | 2004/066856 A1 | 8/2004 |
| WO | WO-2004/093686 | 11/2004 |
| WO | 2005/038745 A1 | 4/2005 |
| WO | WO-2005/058029 | 6/2005 |
| WO | 2006/018686 A1 | 2/2006 |
| WO | WO-2006/018837 | 2/2006 |
| WO | 2006/021851 A1 | 3/2006 |
| WO | WO-2006/025001 | 3/2006 |
| WO | WO-2006/087649 | 8/2006 |
| WO | WO-2006/119572 | 11/2006 |
| WO | WO-2007/051066 | 5/2007 |
| WO | WO-2007/073551 | 6/2007 |
| WO | 2007/093998 A1 | 8/2007 |
| WO | 2008/015523 A2 | 2/2008 |
| WO | WO-2008/039449 | 4/2008 |
| WO | WO-2008050278 | 5/2008 |
| WO | WO-2008/075203 | 6/2008 |
| WO | WO-2008/119054 | 10/2008 |
| WO | WO-2009/055587 | 4/2009 |
| WO | 2009/085466 A1 | 7/2009 |
| WO | WO-2009/081339 | 7/2009 |
| WO | WO-2009/094554 | 7/2009 |
| WO | WO-2010/058292 | 5/2010 |
| WO | WO-2010/082135 | 7/2010 |
| WO | WO-2010/119340 | 10/2010 |
| WO | WO-2010/143072 | 12/2010 |
| WO | WO-2011/013001 | 2/2011 |
| WO | WO-2011/024074 | 3/2011 |
| WO | 2011/045669 A2 | 4/2011 |
| WO | 2011/135458 A3 | 1/2012 |
| WO | 2011/135455 A3 | 3/2012 |

OTHER PUBLICATIONS

Wu et al., "MRImaging of Shear Waves Generated by Focused Ultrasound," Magnetic Resonance in Medicine, vol. 43, pp. 111-115 (2000).

(56) References Cited

OTHER PUBLICATIONS

Heikkila et al., "Simulations of Lesion Detection Using a Combined Phased Array LHMI-Technique,"Ultrasonics, IPC Science and Technology Press Ltd., vol. 48, No. 6-7, pp. 568-573 (Nov. 2008).
Botros et al., "A hybrid computational model for ultrasound phased-array heating in presence of strongly scattering obstacles," IEEE Trans. On Biomed. Eng., vol. 44, No. 11, pp. 1039-1050 (Nov. 1997).
Cain et al., "Concentric-ring and Sector-vortex Phased-array Applicators for Ultrasound Hperthermia," IEEE Trans. On Microwave Theory & Techniques, vol. MTT-34, No. 5, pp. 542-551 (May 1986).
Chen et al., "MR Acoustic Radiation Force Imaging: Comparison of Encoding Gradients.".
Cline et al., "Focused US system for MR imaging-guide tumor ablation," Radiology, v. 194, vol. 3, pp. 731-738 (Mar. 1995).
Cline et al., "MR Temperature mapping of focused ultrasound surgery," Magnetic Resonance in Medicine, vol. 32, No. 6, pp. 628-636 (1994).
Cline et al., "Simultaneous magnetic resonance phase and magnitude temperature maps in muscle," Magnetic Resonance in Medicine, vol. 35, No. 3, pp. 309-315 (Mar. 1996).
Daum et al., "Design and evaluation of a feedback based phased array system for ultrasound surgery," IEEE Trans. Ultrason. Ferroelec. Freq. Control, vol. 45, No. 2, pp. 431-434 (1998).
de Senneville et al., "Real-time adaptive methods for treatment of mobile organs by MRI-controlled high-intensity focussed Ultrasound," Magnetic Resonance in Medicine 57:319-330 (2007).
Fjield et al, "The Combined Concentric-ring and Sector-vortex Phased Array for MRI Guided Ultrasound Surgery," IEEE Trans. On Ultrasonics, Ferroelectrics and Freq. Cont., vol. 44, No. 5, pp. 1157-1167 (Sep. 1997).
Herbert et al., "Energy-based adaptive focusing of waves: application to ultrasonic transcranial therapy," 8th Intl. Symp. On Therapeutic Ultrasound.
Huber et al., "A New Noninvasive Approach in Breast Cancer Therapy Using Magnetic Resonance Imaging-Guided Focussed Ultrasound Surgery," Cancer Research 61, 8441-8447 (Dec. 2001).
Jolesz et al., "Integration of interventional MRI with computer-assisted surgery," J. Magnetic Resonance Imaging. 12:69-77 (2001).
Kohler et al., "Volumetric HIFU Ablation guided by multiplane MRI thermometry," 8th Intl. Symp. On Therapeutic Ultrasound, edited by E.S. Ebbini, U. of Minn. (Sep. 2009).
Kowalski et al., "Optimization of electromagnetic phased-arrays for hyperthermia via magnetic resonance temperature estimation," IEEE Trans. On Biomed. Eng., vol. 49, No. 11, pp. 1229-1241 (Nov. 2002).
Maxwell et al., "Noninvasive thrombolysis using pulsed ultrasound cavitation therapy—Histotripsy," Abstract, U.S. Natl. Lib. Of Med., NIH, Ultrasound Med. Biol. (Oct. 23, 2009).
McDannold et al., "MRI evaluation of thermal ablation of tumors and focused ultrasounds," JMRI vol. 8, No. 1, pp. 91-100 (1998).
McDannold et al., "Magnetic resonance acoustic radiation force imaging," Med. Phys. vol. 35, No. 8, pp. 3748-3758 (Aug. 2008).
Medel et al., "Sonothrombolysis: An emerging modality for the management of stroke," Neurosurgery, vol. 65, No. 5, pp. 979-993.
Mougenot et al., "MR monitoring of the near-field HIFU heating," 8th Intl. Symp. On Therapeutic Ultrasound, edited by E.S. Ebbini, U. of Minn. (Sep. 2009).
Vimeux et al., "Real-time control of focused ultrasound heating based on rapid MR thermometry," Investig. Radiology, vol. 43, No. 3, pp. 190-193.
Vykhodtseva et al., "MRI detection of the thermal effects of focused ultrasound on the brain," Ultrasound in Med. & Biol., vol. 26, No. 5, pp. 871-880 (2000).
"How is Ablatherm treatment performed?" http://www.edap-hifu.com/eng/physicians/hifu/3c_treatment_treat-description.htm, accessed Jan. 3, 2003.
"What is HIFU? HIFU: High Intensity Focused Ultrasound," http://www.edap-hifu.com/eng/physicians/hifu2a_hifu_overview.htm, accessed Jan. 3, 2003.
"What are the physical principles?" http://www.edap-hifu.com/eng/physicians/hifu/2c_hifu_physical.htm, accessed Jan. 3, 2003.
"How does HIFU create a lesion?" http://www.edap-hifu.com/eng/physicians/hifu/2d_hifu_lesion.htm, accessed Jan. 3, 2003.
"Prostate Cancer Phase I Clinical Trials Using High Intensity Focused Ultrasound (HIFU)," Focus Surgery, http://www.focus-surgery.com/PCT%20Treatment%20with%20HIFU.htm, accessed Jan. 3, 2003.
"Abstract"Focus Surgery, http://www.focus-surgery.com/Sanghvi.htm, accessed Jan. 3, 2003.
Exablate 2000 Specification, InSightec, Ltd. (2 pages).
FDA Approves Exablate 2000 as Non-invasive surgery for Fibroids, Oct. 22, 2004.
McGough et al., "Direct Computation of Ultrasound Phased-Array Driving Signals from a Specified Temperature Distribution for Hyperthermia," IEEE TRansactions on Biomedical Engineering, vol. 39, No. 8, pp. 825-835 (Aug. 1992).
Partial Search Report mailed Mar. 11, 2011 for International Application No. PCT/IB2010/002265 (4 pages).
McDonnald et al. "Usefulness of MR Imaging-Derived Thermometry and Dosimetry in Determining the Threshold for Tissue Damage INduced by Thermal Surgery in Rabbits," Radiology, vol. 216, No. 2000 pp. 517-523 (2000).
Suprijanto et al. "Displacement Correction Scheme for MR-Guided Interstitial Laser Therapy," Ellis RE, Peters TM (Eds.): MiCCAI, LNCS 2879, pp. 399-407 (2003).
Shmatukha et al. "Correction of Proton Resonance Frequencey Shift Temperature Maps for Magnetic Field Disturbances Caused by Breathing," Physics in Medicine and Biology, vol. 51, No. 18 pp. 4689-4705 (2006).
De Senneville et al., "An Optimised Multi-Baseline Approach for On-Line MR-Temperature Monitoring on Commodity Graphics Hardware," Biomedical Imaging, pp. 1513-1516 (2008).
Vigen et al., "Triggered, Navigated, Multi-Baseline Method for Proton Resonance Frequency Temperature Mapping with Respiratory Motion," Magnetic Resonance in Medicine, vol. 50, pp. 1003-1010 (2003).
International Search Report and Written Opinion mailed Jun. 22, 2011 for International Application No. PCT/IB2010/002265 (17 pages).
"Body Sculpting/Liposuction", available online at<http://www.cosmeticdoctor.com/sculpting.htm>, retrieved on Mar. 17, 2000, pp. 1-3.
"External Ultrasonic Liposuction", available online at <http://www.lipoinfo.conn/chap14..htm.>, retrieved on Mar. 17, 2000.
"For Ultrasonic Liposuction", available online at <http://www.ultrasonic-liposuction.com/index.html>, retrieved on Mar. 17, 2000, 1 page.
"Glossary", available online at <http://www.lipoinfo.com/glossary.htm>, retrieved on Mar. 17, 2000, pp. 1-14.
"Internal, External Ultrasound Aids Liposuction", available online at<http://surgery.medscape.com/IMNG/SkinAllergyNews/1998/v.29.n03/san2903.46.01.html> retrieved on Mar. 17, 2000, pp. 1-3.
"Liposuction", available online at <http://www.swmed.edu/home.sub.—pages/library/consunner/liposuc.htm>, retrieved on Mar. 17, 2000, 1 page.
"Liquefying the Fat: Ultrasound Expands Score of Liposuction", available online at <http://www.swmed.edu/home.sub.—pages/new/liquilip.htm>, retrieved on Mar. 17, 2000, pp. 1-2.
"The Lipo Symposium", available online at <http://liposymposium.com/details/History/>, retrieved on Mar. 17, 2000, 1 page.
"Trends in Cosmetic Surgery: Lipoplasty (Liposuction)", available online at <http://www.wrc-gbmc.org/4rd.html>, retrieved on Mar. 17, 2000, 1 page.
"Ultrasonic Liposuction; Body Contouring", available online at <http://www.drloomis.com/serv01.htm,>, retrieved on Mar. 17, 2000, pp. 1-2.
"Ultrasonic-Assisted Liposuction", available online at <http://www.liposymposium.com/details/procedure/techniqus/UAL/>, retrieved on Mar. 17, 2000, pp. 1-2.
"Ultrasound Assisted Lipoplasty", available online at <http://www.plasticsurgery.org/surgery/ual.htm>, retrieved on Mar. 17, 2000, pp. 1-4.
"Ultrasound -Assisted Liposuction", available online at <http://www.drhobar.com/ual.htm>, retrieved on Mar. 17, 2000, pp. 1-4.

(56) References Cited

OTHER PUBLICATIONS

"Ultrasound Liposuction or Ultrasound Assisted Lipoplasty -UAL", available online at <http://www.ultrasonic-liposuction.com/InformationD.html>, retrieved on Mar. 17, 2000, pp. 1-2.
"Ultrasound-Assisted Liposuction", available online at <http://www.providence-hospital.org/technology/lipo.htm>, retrieved on Mar. 17, 2000, 1 page.
International Application Serial No. PCT/IB2003/005551, International Search Report mailed on Mar. 9, 2004, 3 pages.
International Application Serial No. PCT/IB2003/005551, International Written Opinion mailed on Sep. 1, 2004.
International Application Serial No. PCT/IB2004/001498, International Search Report and Written Opinion mailed Aug. 31, 2004, 8 pages.
International Application Serial No. PCT/IB2004/001512, filed on May 11, 2004,International Preliminary Report on Patentability mailed on Nov. 25, 2005, 5 pages.
International Application Serial No. PCT/IB2004/001512, International Search Report and Written Opinion mailed on Sep. 7, 2004, 7 pages.
International Application Serial No. PCT/IB2005/002273, International Search Report and Written Opinion mailed on Dec. 20, 2005, 6 pages.
International Application Serial No. PCT/IB2005/002413, International Search Report and Written Opinion mailed on Nov. 22, 2005, 8 pages.
International Application Serial No. PCT/IB2006/001641, International Search Report and Written Opinion mailed on Sep. 25, 2006, 8 pages.
International Application Serial No. PCT/IB2006/003300, International Search Report and Written Opinion mailed on Feb. 14, 2008, 7 pages.
International Application Serial No. PCT/IB2007/001079, International Search Report and Written Opinion mailed on Dec. 10, 2007, 11 pages.
International Application Serial No. PCT/IB2007/001079, Partial International Search Report and Written Opinion mailed on Sep. 25, 2007.
International Application Serial No. PCT/IB2007/002134, International Search Report and Written Opinion mailed on Dec. 13, 2007, 8 pages.
International Application Serial No. PCT/IB2007/002140, International Search Report and Written Opinion mailed on Dec. 29, 2008, 7 pages.
International Application Serial No. PCT/IB2008/003069, International Search Report and Written Opinion mailed on Apr. 27, 2009, 10 pages.
International Application Serial No. PCT/IB2010/000189, International Search Report and Written Opinion mailed on Jun. 1, 2010, 11 pages.
International Application Serial No. PCT/IB2010/000971, International Search Report and Written Opinion mailed on Jul. 29, 2010, 9 pages.
International Application Serial No. PCT/IB2010/002757, International Preliminary Report on Patentability issued on Apr. 17, 2012, 10 pages.
International Application Serial No. PCT/IB2010/002757, International Search Report and Written Opinion mailed on Sep. 7, 2011, 15 pages.
International Application Serial No. PCT/IL2001/000340, International Written Opinion mailed on Feb. 24, 2003.
International Application Serial No. PCT/IL2002/000477, International Written Opinion mailed on Feb. 25, 2003, 9 pages.
Examination Report in Chinese Patent Application No. 200980153997.1, mailed on Apr. 15, 2014, 7 pages.
Examination Report in Chinese Patent Application No. 201080011633.2, mailed on Oct. 8, 2013, 9 pages.
Examination Report in Chinese Patent Application No. 200680029730.8, mailed on Apr. 29, 2010, 7 pages.
Bates, B, "External Ultrasound's Liposuction Role Debated", Available Online at < http://molecularmedicine.medscape.com/IMNG/SkinAllergyNews/19 . . ./san3003. 06.02.htm>, retrieved on Mar. 17, 2000, pp. 1-2.
Daum et al., "Thermal Dose Optimization Via Temporal Switching in Ultrasound Surgery", IEEE Transactions on Ultrasonics, Ferroelectrics, and Frequency Control, vol. 45, No. 1, Jan. 1998, pp. 208-215.
Eisenhauer, K, "6/24-Ultrasound Liposuction", available online at <http://www.channel6000.com/health/health-990624-191707.html>, retrieved on Mar. 17, 2000, pp. 1-2.
Fjield et al., "Low-Profile Lenses for Ultrasound Surgery", Physics in Medicine and Biology, vol. 44, No. 7, Jul. 1999, pp. 1803-1813.
Hynynen et al., "Principles of MR-Guided Focused Ultrasound", Chapter 25, pp. 237-243, 1999.
Examination Report in Japanese Patent Application No. 2011-536968, mailed on Oct. 21, 2013, 18 pages.
Lipoinfo.com, "Glossary 70 words", available online at <http://www.lipoinfo.com/glossary.htm>, retrieved on Mar. 17, 2000, pp. 1-14.
Nigro, D M., "Ultrasound Assisted Lipoplasty (Liposuction)", available online at <http://www.drnigro.com/dennis.htm,>, retrieved on Mar. 17, 2000, 1 page.
International Application Serial No. PCT/IB2011/001293, International Preliminary Report on Patentability mailed on Nov. 8, 2012, 9 pages.
International Application Serial No. PCT/IB2011/001293, International Search Report and Written Opinion mailed on Dec. 19, 2011, 12 pages.
International Application Serial No. PCT/IB2011/001375, International Preliminary Report on Patentability mailed on Nov. 8, 2012, 9 pages.
International Application Serial No. PCT/IB2011/001375, International Search Report and Written Opinion mailed on Nov. 10, 2012, 12 pages.
Examination Report Received for European Patent Application No. 05773991.4, mailed on Nov. 2, 2012, 5 pages.
Examination Report Received for European Patent Application No. 06820942.8, mailed on Dec. 11, 2014, 5 pages.
Examination Report Received for European Patent Application No. 07804649.7, mailed on Feb. 17, 2015, 5 pages.
Examination Report Received for European Patent Application No. 10720818.3, mailed on Sep. 11, 2012, 3 pages.
Examination Report Received for European Patent Application No. 10785194.1, mailed on Jan. 22, 2015, 5 pages.
Examination Report Received for European Patent Application No. 11743607.1, mailed on Sep. 18, 2013, 3 pages.
Examination Report Received for European Patent Application No. 11743611.3, mailed on Dec. 19, 2014, 5 pages.
Examination Report Received for Chinese Patent Application No. 201180032003.8, mailed on Nov. 21, 2014, 7 pages. (Official copy only) (In accordance with 37 CFR § 1.98(a) (3)).
Examination Report Received for Chinese Patent Application No. 200980153997.1, mailed on Oct. 20, 2014, 8 pages. (English Translation only).
Examination Report Received for European Patent Application No. 10709054.0, mailed on Dec. 22, 2014, 4 pages.
PCT International Patent Application No. PCT/IB2010/002143, International Preliminary Report on Patentability issued on Jan. 31, 2012, 8 pages.
PCT International Patent Application No. PCT/IB2010/002265, International Preliminary Report on Patentability issued on Feb. 28, 2012, 11 pages.

* cited by examiner

ASYMMETRIC ULTRASOUND PHASED-ARRAY TRANSDUCER FOR DYNAMIC BEAM STEERING TO ABLATE TISSUES IN MRI

CROSS-REFERENCE TO RELATED APPLICATION

This application claims priority to and the benefit of, and incorporates herein by reference in its entirety, U.S. Provisional Patent Application No. 61/237,054, which was filed on Aug. 26, 2009.

FIELD OF THE INVENTION

The present invention relates generally to phased-array ultrasound transducer systems and methods of using same, and more specifically to asymmetric transducer configurations for application-specific ultrasound delivery.

BACKGROUND

Focused ultrasound (i.e., acoustic waves having a frequency greater than about 20 kilohertz) can be used to image internal body tissues or, at high intensity, to generate thermal ablation energy to treat tissue such as tumors. By way of illustration, FIG. 1 is a simplified schematic representation of an exemplary focused ultrasound system 100 used to generate and deliver a focused acoustic energy beam 102 to a targeted tissue mass 104 in a patient 106. The system 100 employs an ultrasound transducer 108 that is geometrically shaped and physically positioned relative to the patient 106 in order to focus the ultrasonic energy beam 102 at a three-dimensional focal zone located within the targeted tissue mass 104. The transducer 108 may be substantially rigid, semi-rigid, or substantially flexible, and can be made from a variety of materials, such as plastics, polymers, metals, and alloys. The transducer 108 can be manufactured as a single unit, or, alternatively, be assembled from a plurality of components. While the illustrated transducer 108 has a "spherical cap" shape, a variety of other geometric shapes and configurations may be employed to deliver a focused acoustic beam, including other non-planar as well as planar (or linear) configurations. The dimensions of the transducer may vary, depending on the application, between millimeters and tens of centimeters.

The transducer 108 may include a large number of transducer elements 110, arranged in a one- or two-dimensional array or other regular manner, or in an uncoordinated fashion. These elements 110 convert electronic drive signals into mechanical motion and, as a result, into acoustic waves. They may be made, for example, of piezoelectric ceramics or piezo-composite materials, and may be mounted in silicone rubber or another material suitable for damping the mechanical coupling between the elements 110. The transducer elements 110 are connected via electronic drive signal channels 112 to a control module 114, which drives the individual transducer elements 110 so that they collectively produce a focused ultrasonic beam. More specifically, the control module 114 may include a beamformer 116 that sets the relative amplitudes and phases of the drive signals in channels 112. In conventional focused ultrasound systems containing n transducer elements, the beamformer 116 typically contains n amplifiers 118 and n phase control circuits 120, each pair driving one of the transducer elements 110. The beamformer 116 receives a radio frequency (RF) input signal, typically in the range from 0.1 MHz to 3 MHz, from frequency generator 122. The input signal may be split into n channels for the n amplifiers and phase circuits 118, 120 of the beamformer 116. Thus, in typical conventional systems, the radio frequency generator 122 and the beamformer 116 are configured to drive the individual elements 110 of the transducer 108 at the same frequency, but at different phases and different amplitudes, such that the transducer elements 110 collectively form a "phased array."

The acoustic waves transmitted from the transducer elements 110 form the acoustic energy beam 102. Typically, the transducer elements are driven so that the waves converge at a focal zone in the targeted tissue mass 104. Within the focal zone, the wave energy of the beam 102 is (at least partially) absorbed by the tissue, thereby generating heat and raising the temperature of the tissue to a point where the cells are denatured and/or ablated. The location, shape, and intensity of the focal zone of the acoustic beam 102 is determined, at least in part, by the physical arrangement of the transducer elements 110, the physical positioning of the transducer 108 relative to the patient 106, the structure and acoustic material properties of the tissues along the beam path between the transducer 108 and the target tissue 104, and the relative phases and/or amplitudes of the drive signals. Setting the drive signals so as to focus the acoustic energy at a desired location is a process known as "electronic steering" of the beam 102. The amplification or attenuation factors $\alpha$ and the phase shifts $\phi$ imposed by the beamformer 116 and used to steer the beam are computed in a controller 124, which may provide the computational functions through software, hardware, firmware, hardwiring, or any combination thereof. For example, the controller 124 may utilize a special-purpose digital signal processor or a general-purpose computer programmed with software in a conventional manner. In certain embodiments, the computation is based on image data obtained with a magnetic resonance imaging (MRI) apparatus or other imager (not shown). Further, the controller 124 may be in communication with a user interface 126 that facilitates the selection of the focus location or other treatment parameters.

Phased-array transducers provide the greatest beam-steering capability when each transducer element 110 can be controlled independently through a separate drive signal channel 112, as illustrated in FIG. 1. This flexibility comes, however, at a price, as large numbers of electronic channels are costly. Thus, as the number of elements increases, the ability to drive them independently becomes concomitantly less practical for complexity and cost reasons. To curtail cost increases resulting from larger numbers of transducer elements, many applications exploit system symmetries to drive multiple elements with a single channel. An axis of symmetry may be defined, for example, by the direction of the acoustic beam propagation when all elements of the array are driven in phase. The transducer elements may be connected to (a smaller number of) drive signal channels in a way that reflects, for example, a corresponding radial symmetry around the intersection of this axis with the transducer surface. Such symmetric transducers achieve a reasonable trade-off between high steering capability along one axis (e.g., steering of the focal length at the cost of very limited lateral steering, or vice versa) and low system complexity in many applications. However, they are unduly limiting when the transducer cannot be freely moved, e.g., as a consequence of certain anatomical barriers. Accordingly, there is a need for accommodating large numbers of small transducer elements in any array without the burden of separately driving them, but also without sacrificing the beam focusing and steering capabilities needed in specific clinical applications.

SUMMARY

The present invention relates to ultrasound transducer systems and ultrasound focusing methods that provide sufficient beam-focusing and steering flexibility to accommodate many clinical applications, yet avoid the need to individually control large numbers of transducer elements. In various embodiments, the transducer surface is formed by an isotropic array of transducer elements, each of which receives a drive signal through an electronic signal channel. The transducer elements are sufficiently small and numerous to provide for high beam steerability. To keep system complexity and cost low, however, the transducer elements are grouped, and the elements in each group are driven together so as to limit the total number of independent drive signal channels needed to control the entire array. While the grouping of transducer elements may be hard-wired for certain categories of applications, preferred embodiments accomplish the grouping dynamically, thereby allowing groupings to be adjusted to a particular treatment scenario (e.g., a particular patient anatomy and arrangement of the treatment equipment). For example, an additional layer of switches may be connected to the transducer elements, and based on an analysis of the treatment scenario, these switches may be set so as to define a plurality of transducer-element groups.

In various embodiments, the configuration of the phased-array transducer is asymmetric (e.g., with respect to the beam propagation axis). The grouping of transducer elements may result in two or more transducer regions tailored for particular functions, each including at least one, but typically several, groups of elements. For example, one region may be designed for depth focusing, and another region for lateral beam steering. The different regions may be driven independently or, alternatively, simultaneously to adjust the acoustic beam focusing and steering properties to a specific application. Due to the complementary functionalities of the transducer regions, the transducer array maintains a high degree of flexibility without requiring overly complex controlling mechanisms. In particular, certain embodiments of the invention allow focusing ultrasound into treatment areas which, due to their proximity to anatomical barriers, would not be readily accessible with a symmetric transducer array.

Accordingly, in a first aspect, the invention provides an asymmetric ultrasound transducer with a plurality of ultrasound transducer elements arranged in a two-dimensional (planar or non-planar) phased array including first and second regions. A first plurality of signal channels is connected to and collectively drives the transducer elements of the first region so as to generate a first ultrasound beam and to facilitate focusing that beam at varying focal depths along a focal path in the direction of beam propagation. A second plurality of signal channels is connected to and collectively drives the transducer elements of the second region so as to generate a second ultrasound beam and to facilitate lateral steering of that beam in a direction perpendicular to beam propagation. In certain embodiments, at least some of the signal channels of each of the first and second pluralities of channels are connected to multiple transducer elements of the first region and the second region, respectively. The first region may facilitate focusing the first ultrasound beam at a tissue depth beneath a patient's skin line of less than 4 cm. The second ultrasound beam may have a steerability greater than 1 radian. In some embodiments, the first and second regions are configured to facilitate steering of the first and second ultrasound beams into first and second selected volumes, respectively. When both regions are operated simultaneously, they may generate a third ultrasound beam and facilitate steering the third ultrasound beam into a third volume that is not entirely within the first and second volumes.

In a second aspect, an asymmetric ultrasound transducer in accordance with various embodiments includes a plurality of ultrasound transducer elements arranged in a two-dimensional (planar or non-planar) phased array, each transducer element having a switch associated with it; a plurality of signal channels connected to the transducer elements via the switches such that at least some of the signal channels are connected to multiple transducer elements; and a controller configuring the switches so as to group the transducer elements. The controller, in grouping transducer elements, forms a first region of the transducer that is capable of focusing at varying focal depths along a focal path in the direction of beam propagation, and a second region that is capable of lateral beam steering (i.e., beam steering in a direction perpendicular to beam propagation). The first and second regions may facilitate beam steering into first and second volumes, respectively.

In a third aspect, the invention provides an asymmetric ultrasound transducer system comprising a plurality of ultrasound transducer elements with associated switches, arranged in a two-dimensional phased array; a plurality of signal channels connected to the transducer elements via the switches; a controller for configuring the switches; means for storing data sets each corresponding to a configuration of the switches; and means facilitating user selection of one of the stored data sets, the controller being responsive to the selection and configuring the switches in accordance therewith. In some embodiments, at least one of the data sets specifies one or more regions of grouped transducer elements capable of shallow focusing and one or more regions of grouped transducer elements capable of lateral beam steering. Further, in some embodiments, at least one of the data sets specifies one or more regions capable of steering an ultrasound beam into a selected volume. In some embodiments, at least one of the data sets specifies one or more regions of grouped transducer elements capable of focusing at varying focal depths along a focal path in the direction of beam propagation and one or more regions of grouped transducer elements capable of lateral beam steering.

In a fourth aspect, a method of configuring an asymmetric ultrasound transducer is provided. The method includes providing a plurality of ultrasound transducer elements arranged in a (planar or non-planar) two-dimensional phased array; dynamically configuring a plurality of signal channels connected to the transducer elements in response to geometric constraints associated with a patient's anatomy and an equipment configuration, thereby producing a plurality of groups of transducer elements; and separately driving the groups of transducer elements. The signal channels may be configured so as to form first and second regions of grouped transducer elements. In some embodiments, the first and second regions are capable of focusing at varying focal depths along a focal path in the direction of beam propagation and of lateral beam steering, respectively. In some embodiments, the first and second regions are capable of beam steering into first and second volumes, respectively.

BRIEF DESCRIPTION OF THE DRAWINGS

The foregoing will me more readily understood from the following detailed description, in particular, when taken in conjunction with the drawings, in which.

DESCRIPTION

Phased-array ultrasound transducers in accordance with various embodiments of the invention enable three-dimensional beam steering, i.e., steering of both the depth of focus and the lateral focus position, over a large volume. Typically, the transducer includes a large number (e.g., hundreds or thousands) of individual transducer elements whose linear dimensions are no greater than the wavelength of the acoustic waves generated during operation. Preferably, the largest dimension of each element is equal to or smaller than half the acoustic wavelength. Using small transducer elements results in high steerability of the acoustic beam. For example, with transducer element dimensions of no more than half a wavelength, the steering angle (i.e., the maximum angle with respect to the normal of the transducer surface that can be achieved) in each direction is $\pm\pi/2$, which facilitates covering a complete hemisphere. In certain embodiments, the transducer elements are of uniform size and shape and are evenly arranged (e.g., in a tiled fashion) so as to form an isotropic array.

Figure 1:
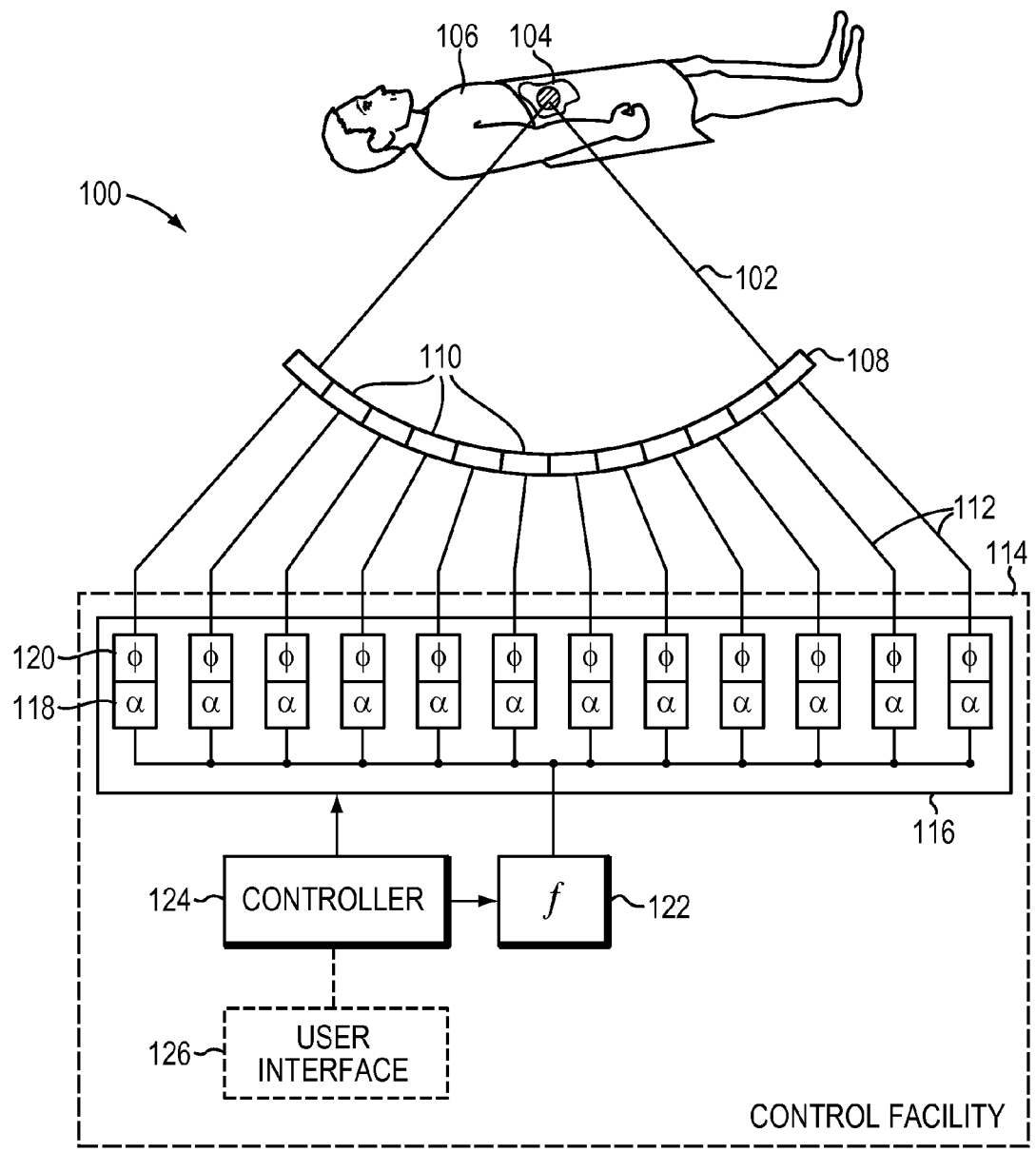
FIG. 1 is a schematic drawing illustrating a focused ultrasound system with independently controllable transducer elements.
Figure 2:
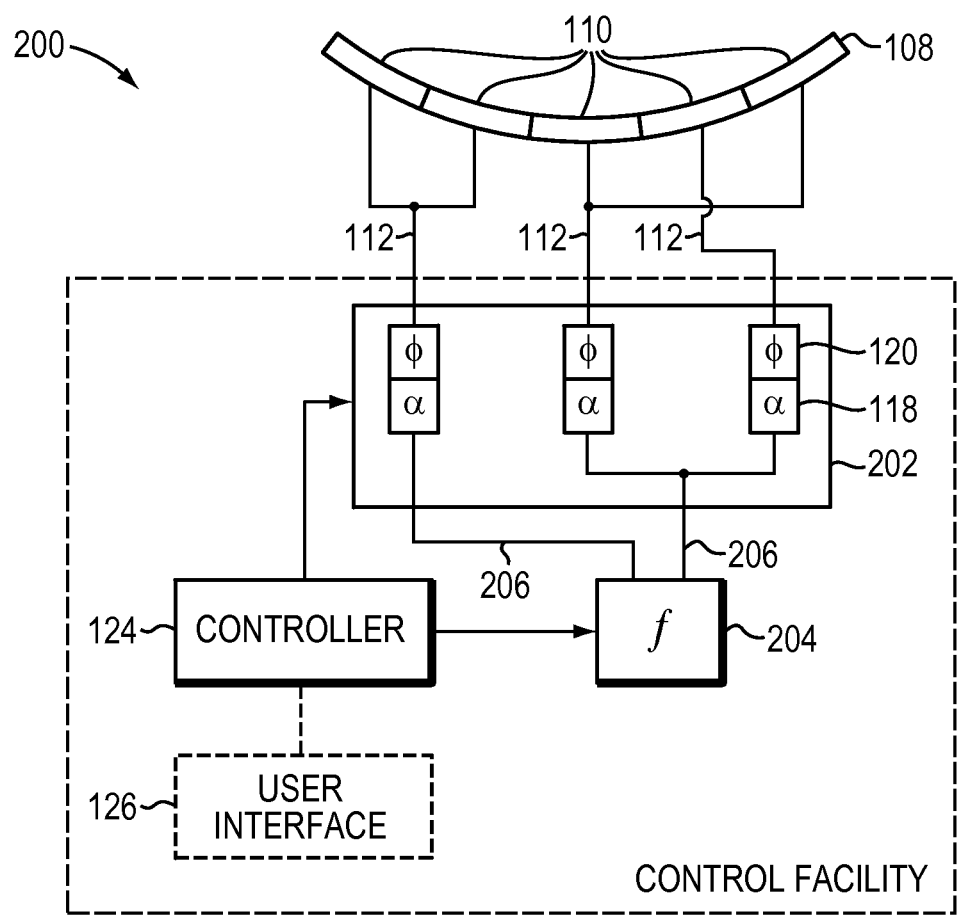
FIG. 2 is a schematic drawing illustrating a focused ultrasound system in accordance with various embodiments in which transducer elements are grouped.

The elements of the transducer array are driven via electronic signals by a control facility. To keep complexity and cost low, the transducer elements may be grouped, and elements within each group wired together so as to receive a drive signal from a single channel. As a consequence, the number of channels may be significantly smaller than the number of transducer elements. An exemplary implementation of such an ultrasound focusing system is conceptually illustrated in FIG. 2A. In the depicted system 200, each element 110 of the ultrasound transducer 108 is connected to an amplifier 118 and phase control circuit 120 via a drive signal channel 112. However, the number of drive signal channels 112 is smaller than the number of transducer elements 110, since at least some of the signal channels 112 are each connected to more than one transducer element 110. As a result, the complexity of the beamformer 202 is reduced (compared with that of a beamformer in a conventional system in which every element is separately controllable).

The elements within each group may form a single contiguous area of the transducer surface, or include multiple non-contiguous surface portions. The grouping of elements may follow different design criteria for various regions of the transducer, and may be adjusted to the functional requirements of the regions. For example, one region may be wired to generate an acoustic beam with a relatively shallow focal depth. For the purposes of most clinical applications, depths in the tissue between the skin line and up to about 2-3 cm deep are considered shallow. Another region may be optimized for lateral steering. Using both of these regions in combination, medium and deep focusing (e.g., up to 6 cm for 2 to 3 MHz) may be achieved. In another embodiment, two regions may be configured to accommodate a range of focal depths and a range of lateral focus positions at a predetermined depth, respectively. Further, different regions may be designed to generate focused acoustic beams covering different volumes in space. If some or all of the regions are driven simultaneously, additional volumes in space may be accessed with the same transducer array, in many cases, in a single sonication. Certain embodiments provide increased beam steering performance within a specified volume by enabling one or more regions of the transducer surface to be used alone while transducer elements in the remaining region(s) are either turned off or driven at amplitudes that are so low that they make only negligible contributions to the total focused energy, or generate a focus at a different place in the target. When the various regions are driven together, on the other hand, the combined ultrasound beam can be focused at a depth where, using only part of the total transducer area, the focus size will be too big. Regions of the transducer array that are designed for different functions may benefit from different operating frequencies. Therefore, in various embodiments, a frequency generator 204 with multiple frequency channels 206 (or, alternatively, a plurality of frequency generators each having one or more channels) may be used to provide the beamformer 202 with two or more input frequencies for the various drive signal channels 112. Typically, the number of frequency channels 206 is smaller than the number of drive signal channels 112. The frequencies provided to the beamformer 202 may be set by the controller 124, which also controls the amplifier and phase circuits 118, 120. The drive signal and acoustic beam frequencies generally vary between about 0.1 MHz and about 3 MHz. A region of the array intended for shallow focusing uses higher frequencies (e.g., frequencies of at least 1.5 MHz) to reduce focus size and to increase the absorption of acoustic energy. A region intended for lateral steering, on the other hand, uses lower frequencies to reduce the ratio of transducer elements size to wavelength to improve the angular response of the transducer. When the entire transducer is used, the deeper into the body the beam is to be focused, the lower the selected frequency will generally be.

Figure 3:
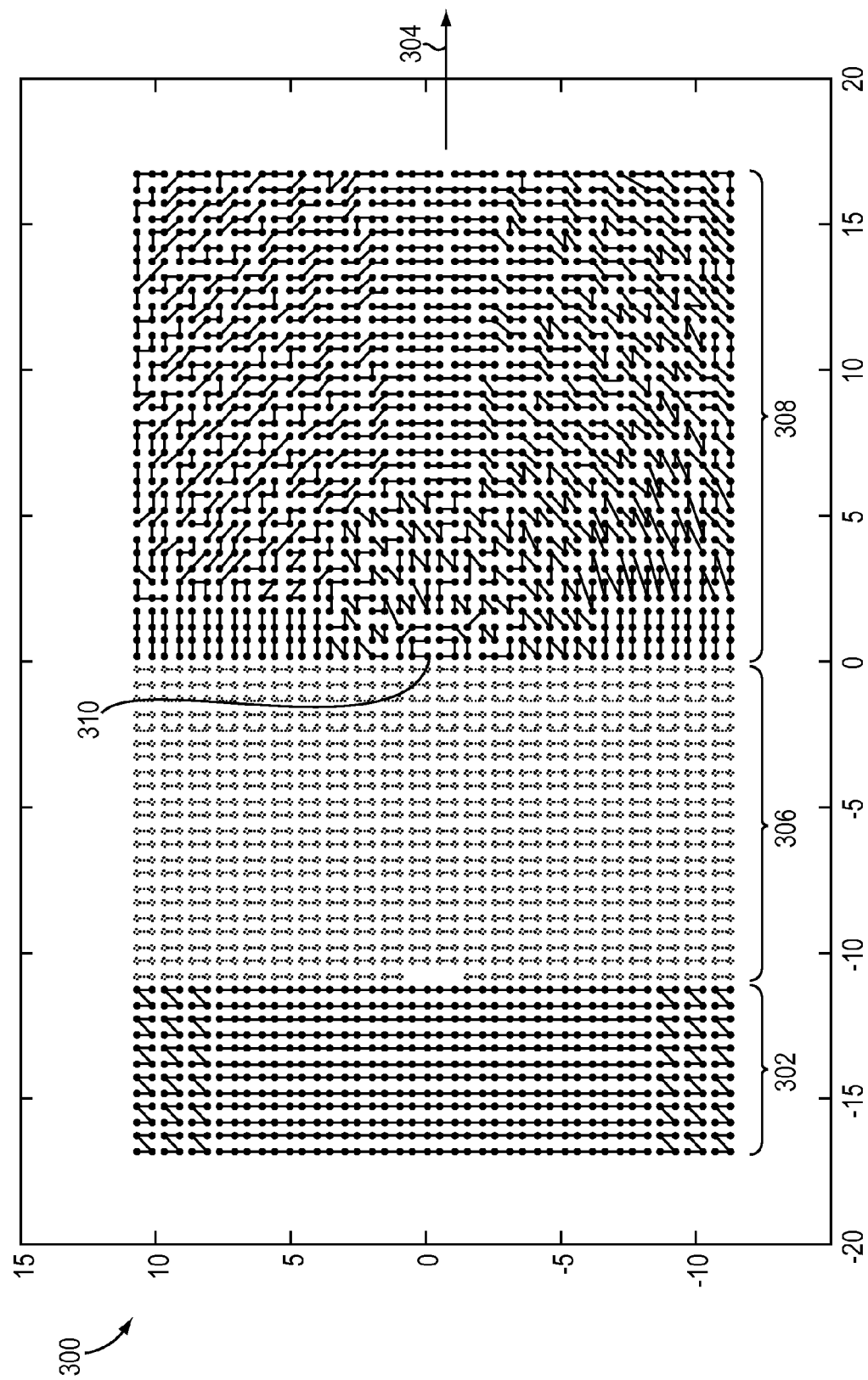
FIG. 3 is a schematic drawing illustrating a transducer-array configuration in accordance with one embodiment.

The individual regions of the array may, but need not, be wired symmetrically to minimize the complexity of the beam former, whereas the transducer as a whole is typically wired asymmetrically to enable different regions of the transducer to cover different volumes. In contrast to symmetric signal channel configurations, which usually involve a trade-off between focal-depth steerability and lateral steerability, asymmetric configurations enable the transducer to accommodate both focal-depth steering and lateral steering requirements. Further, such a design may be better adjusted to the treatment of certain areas of the human anatomy that are themselves highly asymmetrical FIG. 3 schematically illustrates an exemplary transducer 300 in accordance with one embodiment. The transducer is formed by about three thousand transducer elements whose center points (corresponding to the individual points shown in FIG. 3) are arranged equidistantly from each other at lattice points within a rectangular lattice. Such a lattice may be produced, for example, by etching or sawing the discrete transducer elements from a continuous sheet, which results in a tiled arrangement of uniformly sized elements with sub-wavelength dimensions (in the illustrated embodiment, approximately 1 mm). Alternatively, the transducer elements may be manufactured separately and afterwards placed onto a supporting surface. The transducer elements may, generally, vary in size and shape, and may be arranged in a planar or a non-planar array. They are wired to form about 1200 groups of elements (illustrated by lines connecting the points in FIG. 3), each group being driven by an associated signal channel.

In this one particular embodiment, the transducer 300 is configured into three regions. The first region 302 is designed for lateral steering along the long axis 304 of the transducer array (i.e., left/right). Most of its elements are grouped in a direction perpendicular to that axis, with smaller groupings of four elements flanking the boundaries of the array. The center region 306 has planar steering capabilities, enabling steering along both axes of the transducer array (i.e., left/right and up/down). In this region 306, transducer elements are grouped in pairs. Finally, the third region 308, which encompasses half of the transducer area, is optimized for depth focusing around the geometrical center 310 of the transducer. The groupings of transducer elements in this region 308 are substantially radially symmetric about the geometrical center An asymmetric transducer with different functional regions (such as transducer 300) may be used in medical applications where the transducer cannot be arbitrarily moved and tilted with respect to the patient or target tissue. Such a situation may arise due to anatomical barriers or obstacles posed by the particular configuration of treatment equipment. Anatomical barriers, as the term is used herein, may be determined by both physical barriers to the movement of the transducer, as well as by changes in acoustic properties along the beam path due to interfaces between different materials (e.g., air, bone etc.) that will cause reflection or absorption of the acoustic beam. Treatment equipment includes the ultrasound transducer system itself, as well as other equipment that may simultaneously be needed (such as, e.g., an MRI imaging apparatus) and whose locations and space requirements may further restrict the movability of the transducer.

Figure 4:
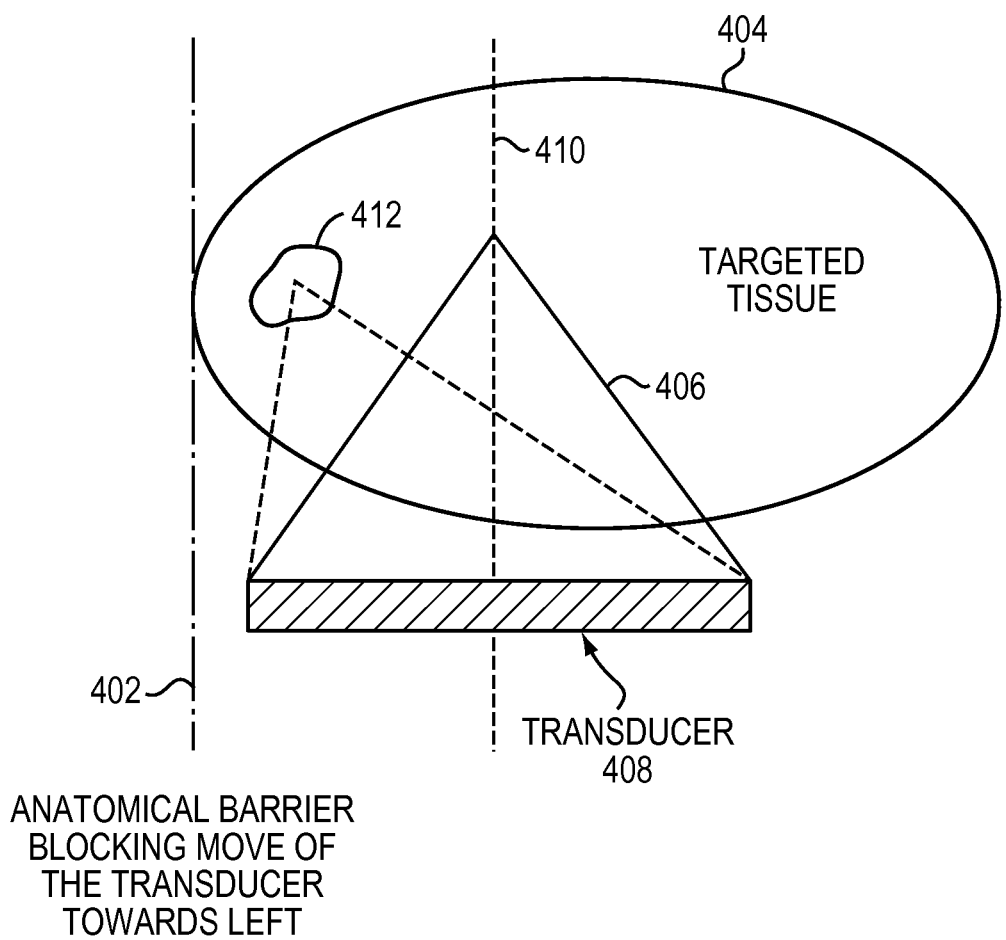
FIG. 4 is a schematic drawing illustrating a treatment scenario in which focused ultrasound systems in accordance with various embodiments can advantageously be used.

FIG. 4 schematically illustrates a treatment scenario in which an anatomical barrier 402 diminishes the portion of a target tissue 404 that can be reached by the ultrasound beam 406. As shown, the anatomical barrier 402 prevents the transducer 408 from being shifted further toward the left in this illustration. A conventional symmetric transducer that focuses ultrasound along a symmetry axis 410 might therefore not be able to reach a region 412, which is located close to the barrier 402. An asymmetric transducer, on the other hand, may be able to overcome the anatomical barrier 402 by beam steering. To accommodate the illustrated constraints, the transducer 408 should be configured to allow significant electronic steering toward the left side to overcome the anatomical barrier 402. The right side requires less steering capability, thereby reducing the required number of independently controllable elements in that region, and, thus, allowing elements to be grouped. The transducer array as a whole preferably provides a large dynamic range of focusing (from shallow focal depth to deep focusing). The transducer array 300 illustrated in FIG. 3 substantially satisfies these requirements, and is therefore suitable for use in the scenario shown in FIG. 4.

Figure 5:
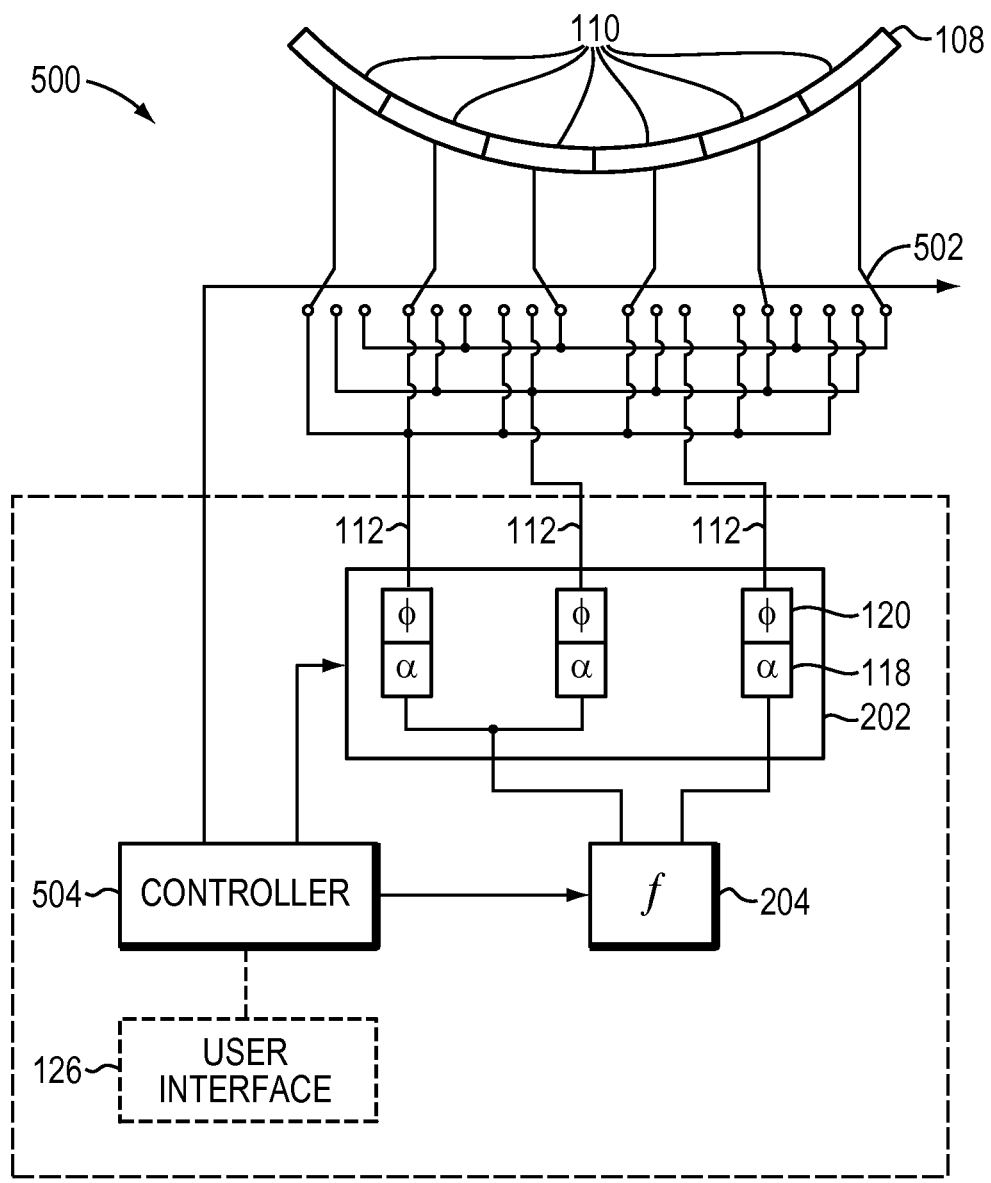
FIG. 5 is a schematic drawing illustrating a focused ultrasound system in accordance with various embodiments in which transducer elements are variably grouped.

In various preferred embodiments, transducer element groupings are not hard-wired, but can be set dynamically to accommodate a variety of treatment scenarios. FIG. 5 illustrates a system that facilitates dynamic groupings by incorporating a layer of switches 502 between the transducer array 108 and the beamformer 202. Via the switches, each transducer element 110 can be connected variably with one of the drive signal channels 112 associated with amplifier and phase control components 118, 120. For example, in the depicted system, the switches have three settings, corresponding to three independent drive signals. (In practice, the number of switch positions and drive channels is typically much larger.) Although switches that facilitate the connection of each transducer element 110 to each drive signal channel 112 provide the greatest degree of flexibility for a given number of elements 110 and channels 112, embodiments of the invention also encompass systems with fewer switch settings, i.e., systems in which the individual transducer elements 110 can only be connected to a subset of signal channels 112. For example, the switches may facilitate selection only between channels that receive the same input frequency from frequency generator 204. Further, in place of simple switches, other channel selection means (such as "cascades"—i.e., multiple layers of serially connected—switches) may be used. In some embodiments, an additional layer of switches (not shown) between the frequency generator 204 and the beamformer 202 facilitates variably connecting the drive signal channels 112 to various frequency channels.

The switches 502 (or alternative channel selection means) that connect the transducer elements to the drive signal channels, as well as any switches for frequency selection, may be set by the controller 504. The controller may, in turn, receive information about the switch settings from a user through the user interface 126. In some embodiments, the controller includes logic or software for computing preferred switch settings based on anatomical barriers and other physical obstacles that may limit movement of the transducer, as well as the beam focus requirements for a particular application. For example, an optimization algorithm may take this information, along with parameters characterizing the transducer array (including, for example, the number, size, shape, and density of elements in the array), as input to produce an optimal grouping pattern and/or determine optimal drive frequencies for each group. The relationship of groupings and relative phase-settings of transducer elements to the resulting steerability of the beam may then be modeled analytically. Thus, the controller facilitates the dynamic adjustment and configuration of elements within the transducer system based on a particular clinical application and a particular desired location of the focus within the anatomy.

In some embodiments of the invention, the element groupings may be determined in advance rather than in a clinical setting. For example, a small number of paradigmatic groupings and driving parameters may be designed that address a significant number of possible treatment regiments, and data representative of these groupings may be stored for future use. The data may be stored, for example, on a hard drive of the controller 504, or on a separate storage unit in communication with the controller 504. The data may specify the number of transducer regions, the element groupings for each region, frequency constraints for each region or group, as well as other operational parameters of the transducers. Any of the stored data sets may be invoked in the clinical setting, when it is determined which configuration is most appropriate given condition to be treated and/or the physical constraints of the treatment regimen. In such cases, a clinician may select the desired configuration, e.g., using the interface 126, and the controller 504 retrieves the data and configures and drives the transducer system accordingly. If the stored configurations are sufficient to cover most situations encountered in a clinical setting, the need for patient-specific configuration may be eliminated or confined to fine-tuning of a selected configuration.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An asymmetric ultrasound transducer comprising:
   (a) the asymmetric ultrasound transducer arranged in a plurality of ultrasound transducer elements in a two-dimensional phased array comprising at least a first region of a first plurality of rows and columns of grouped transducer elements extending over a first contiguous area and including only transducer elements of the first region and a second region of a second plurality of rows and columns of grouped transducer elements extending over a second contiguous area, wherein the second contiguous area is different from and not overlapping with the first contiguous area, and the second contiguous area including only transducer elements of the second region;
   (b) a first plurality of signal channels connected to and collectively driving the transducer elements of the first region, and the signal channels are configured to generate a first ultrasound beam and a first focus, the elements within each group being connected to the same signal channel and the elements configured to be driven together with the same drive signal; and
   (c) a second plurality of signal channels connected to and collectively driving the transducer elements of the second region and the signal channels are configured to generate a second ultrasound beam and a second focus, the elements within each group being connected to the same signal channel and the elements configured to be driven together with the same drive signal,
      wherein (i) the first region, by virtue of the grouping of transducer elements, is configured to continuously vary focal depths of the first focus along a focal path in the direction of propagation of the first beam via adjusting relative phases between the drive signals of different groups of elements,
      (ii) the second region, by virtue of the grouping of transducer elements, is configured to laterally shift the second focus of the second ultrasound beam in a direction perpendicular to propagation of the second beam by laterally steering the second beam, whereby a direction of propagation of the second beam relative to the ultrasound transducer is changed and
      (iii) the first and second foci are generated simultaneously;
   (d) the asymmetric ultrasound transducer configured to ablate tissues [0003], [00051] and configured to provide simultaneous treatment with other treatment equipment [0024].

2. The asymmetric ultrasound transducer of claim 1, wherein the two-dimensional phased array is planar.

3. The asymmetric ultrasound transducer of claim 1, wherein the two-dimensional phased array is non-planar.

4. The asymmetric ultrasound transducer of claim 1, wherein the first region is configured to steer the first ultrasound beam into a first selected volume and the second region is configured to steer the second ultrasound beam into a second selected volume.

5. The asymmetric ultrasound transducer of claim 4, wherein the first and second regions generate a third ultrasound beam and a third focus thereof and steer the third beam into a third volume, the third volume being different from the first and second volumes.

6. The asymmetric ultrasound transducer of claim 1, wherein the first region is configured to focus the first ultrasound beam at a tissue depth beneath a patient's skin line of less than 4 cm.

7. The asymmetric ultrasound transducer of claim 1, wherein the second ultrasound beam has a lateral steerability greater than 0.1 radians.

8. The asymmetric ultrasound transducer of claim 1, wherein the connections of the first plurality of signal channels to the grouped transducer elements of the first region and the connections of the second plurality of signal channels to the grouped transducer elements of the second region are hardwired.

9. An asymmetric ultrasound transducer, comprising:
   (a) the asymmetric ultrasound transducer arranged in a plurality of ultrasound transducer elements in a two-dimensional phased array, each transducer element having at least one switch associated therewith;
   (b) a plurality of signal channels connected to the transducer elements via the switches, at least some of the signal channels being connected to multiple transducer elements; and
   (c) a computer is configured to set the switches to group the transducer elements, the computer is further configured to form a first region and a second region of grouped transducer elements, wherein the first region comprising a first plurality of rows and columns of grouped transducer elements extending over a first contiguous area and including only transducer elements of the first region and the second region comprising a second plurality of rows and columns of grouped transducer elements extending over a second contiguous area, wherein the second contiguous area is different from and not overlapping with the first contiguous area, and the second contiguous area including only transducer elements of the second region, wherein the elements within each group being connected to the same signal channel and thereby driven together with the same drive signal,
      wherein (i) the first region is configured, by virtue of the groupings, to generate a first ultrasound beam and a first focus thereof and continuously vary focal depths of the first focus along a focal path in the direction of propagation of the first beam via adjusting relative phases between the drive signals of different groups of elements,
      (ii) the second region is configured, by virtue of the groupings, to generate a second ultrasound beam and a second focus thereof and laterally shift the focus in a direction perpendicular to propagation of the second beam by laterally steering the second beam, whereby a direction of propagation of the second beam relative to the ultrasound transducer is changed, and
      (iii) the first and second foci are generated simultaneously
   (d) the asymmetric ultrasound transducer configured to ablate tissues and configured to provide simultaneous treatment with other treatment equipment.

10. The asymmetric ultrasound transducer of claim 9, wherein the two-dimensional phased array is planar.

11. The asymmetric ultrasound transducer of claim 9, wherein the two-dimensional phased array is non-planar.

12. The asymmetric ultrasound transducer of claim 9, wherein the first region is configured to steer the first beam into a first selected volume and the second region is configured to steer the beam into a second selected volume.

13. An ultrasound transducer system, comprising:
   (a) the asymmetric ultrasound transducer arranged in a plurality of ultrasound transducer elements in a two-dimensional phased array, each transducer element having at least one switch associated therewith;

(b) a plurality of signal channels connected to the transducer elements via the switches;
(c) a controller configuring the switches so as to group the transducer elements, the elements within each group being connected to the same signal channel and thereby driven together with the same drive signal;
(d) a hard drive for storing data sets where each data sets corresponds to a configuration of the switches; and
(e) user interface for facilitating user selection of one of the stored data sets, the controller being responsive to the selection and configuring the switches in accordance therewith,
wherein (i) a first set of grouped elements, comprising a first plurality of rows and columns of grouped elements extending over a first contiguous area of the array and including only transducer elements of the first contiguous area, is configured to generate a first ultrasound beam and a first focus thereof and continuously vary focal depths of the first focus within a first range of focal depths via adjusting relative phases between the drive signals of different groups of elements,
(ii) a second set of grouped elements, comprising a second plurality of rows and columns of grouped elements extending over a second contiguous area, wherein the second contiguous area is different from and not overlapping with the first contiguous area, of the array and the second contiguous area including only transducer elements of the second contiguous area, the grouped elements is configured to generate a second ultrasound beam and a second focus thereof and continuously vary focal depths of the second focus within a second range of focal depths via adjusting relative phases between the drive signals of different groups of elements, the second range being different from the first range, and
(iii) the first and second foci are generated simultaneously
the asymmetric ultrasound transducer configured to ablate tissues and configured to provide simultaneous treatment with other treatment equipment.

14. The system of claim 13 wherein at least one of the data sets specifies a configuration of the switches that configures the first set of grouped transducer elements to steer an ultrasound beam into a selected volume.

15. The system of claim 13 wherein the first range of focal depths corresponds to tissue depth beneath a patient's skin line of less than 4 cm.

16. The system of claim 15 wherein at least one of the data sets specifies a configuration of the switches that configures the second set of grouped transducer elements to laterally steer the beam.

17. A method of configuring an asymmetric ultrasound transducer, the method comprising:

(a) the asymmetric ultrasound transducer arranged in providing a plurality of ultrasound transducer elements in a two-dimensional phased array;
(b) dynamically configuring, in response to geometric constraints associated with a patient's anatomy and an equipment configuration, a plurality of signal channels connected to the transducer elements and the signal channels configured to produce a plurality of groups of transducer elements, the elements within each group being connected to the same signal channel and thereby driven together with the same signal; and
(c) separately driving the groups of transducer elements,
whereby (i) a first set of grouped elements, comprising a first plurality of rows and columns of grouped elements extending over a first contiguous area of the array and including only transducer elements of the first contiguous area, is configured to generate a first ultrasound beam and a first focus thereof and continuously vary focal depths of the first focus within a first range of focal depths via adjusting relative phases between the drive signals of different groups of elements,
(ii) a second set of grouped elements, comprising a second plurality of rows and columns of grouped elements extending over a second contiguous area, wherein the second contiguous area is different from and not overlapping with the first contiguous area, of the array and the second contiguous area including only transducer elements of the second contiguous area, the grouped elements is configured to generate a second ultrasound beam and a second focus thereof and continuously vary focal depths of the second focus within a second range of focal depths via adjusting relative phases between the drive signals of different groups of elements, the second range being different from the first range, and
(iii) the first and second foci are generated simultaneously
the asymmetric ultrasound transducer configured to ablate tissues and configured to provide simultaneous treatment with other treatment equipment.

18. The method of claim 17, wherein step (a) comprises providing the plurality of ultrasound transducer elements arranged in a planar two-dimensional phased array.

19. The method of claim 17, wherein step (a) comprises providing the plurality of ultrasound transducer elements arranged in a non-planar two-dimensional phased array.

20. The method of claim 17, wherein the first set of grouped elements is configured to steer the beam into a first selected volume and the second set of grouped elements is configured to steer the beam into a second selected volume.

\* \* \* \* \*